US011020326B2

(12) United States Patent
Watanabe et al.

(10) Patent No.: US 11,020,326 B2
(45) Date of Patent: Jun. 1, 2021

(54) HOLLOW PARTICLES AND COSMETIC

(71) Applicant: JGC CATALYSTS AND CHEMICALS LTD., Kanagawa (JP)

(72) Inventors: Satoshi Watanabe, Fukuoka (JP); Naoyuki Enomoto, Fukuoka (JP); Ikuko Shimazaki, Fukuoka (JP); Kenichi Suemitsu, Fukuoka (JP)

(73) Assignee: JGC CATALYSTS AND CHEMICALS LTD., Kanagawa (JP)

( * ) Notice: Subject to any disclaimer, the term of this patent is extended or adjusted under 35 U.S.C. 154(b) by 0 days.

(21) Appl. No.: 16/617,677

(22) PCT Filed: May 25, 2018

(86) PCT No.: PCT/JP2018/020149
§ 371 (c)(1),
(2) Date: Nov. 27, 2019

(87) PCT Pub. No.: WO2018/221406
PCT Pub. Date: Dec. 6, 2018

(65) Prior Publication Data
US 2020/0179244 A1 Jun. 11, 2020

(30) Foreign Application Priority Data

May 31, 2017 (JP) .............................. JP2017-108323

(51) Int. Cl.
*A61K 8/02* (2006.01)
*A61K 8/25* (2006.01)
*A61Q 1/12* (2006.01)
*C01B 33/12* (2006.01)

(52) U.S. Cl.
CPC ............ *A61K 8/0279* (2013.01); *A61K 8/025* (2013.01); *A61K 8/25* (2013.01); *A61Q 1/12* (2013.01); *C01B 33/12* (2013.01); *C01P 2006/12* (2013.01)

(58) Field of Classification Search
CPC ........ A61K 8/0279; A61K 8/25; A61K 8/025; A61Q 1/12; C01P 2006/02
See application file for complete search history.

(56) References Cited

U.S. PATENT DOCUMENTS

| 2005/0118220 A1 | 6/2005 | Miyazaki et al. |
| 2010/0247914 A1 | 9/2010 | Enomoto et al. |
| 2018/0105422 A1 | 4/2018 | Yu et al. |

FOREIGN PATENT DOCUMENTS

| JP | 4-9319 A | | 1/1992 |
| JP | 7-196312 A | | 8/1995 |
| JP | 2002-265257 A | | 9/2002 |
| JP | 2009-137806 A | | 6/2009 |
| JP | 2011-256098 A | | 12/2011 |
| JP | 2012-140286 A | | 7/2012 |
| JP | 2012140286 | * | 7/2012 |
| JP | 2013-82599 A | | 5/2013 |
| JP | 2013-231010 A | | 11/2013 |
| JP | 2017-88438 A | | 5/2017 |
| WO | 2004/006873 A1 | | 1/2004 |
| WO | 2007/037202 A1 | | 4/2007 |
| WO | 2015/050243 A1 | | 4/2015 |
| WO | 2016/164987 A1 | | 10/2016 |
| WO | 2016164987 A1 | * | 10/2016 |

OTHER PUBLICATIONS

International Search Report issued in corresponding International Patent Application No. PCT/JP2018/020149 dated Aug. 7, 2018 (with English translation).
Extended European Search Report issued in corresponding European Patent Application No. 18 81 0761 dated Apr. 6, 2020.

* cited by examiner

*Primary Examiner* — Carlos A Azpuru
(74) *Attorney, Agent, or Firm* — Troutman Pepper Hamilton Sanders LLP

(57) ABSTRACT

The hollow particles according to the present invention has a balloon structure which includes a cavity inside a shell, and include convex portions with a size of 3 to 100 nm on the surface. The particles have a true specific gravity of 0.3 to 3.0 g/cm$^3$, a specific surface area (m$^2$/cm$^3$) per unit volume calculated by a BET method of not less than 0.5 and less than 60, and an average particle diameter ($d_1$) of 1 to 20 μm. Cosmetics containing such hollow particles have a soft texture property similar to plastic beads.

5 Claims, No Drawings

HOLLOW PARTICLES AND COSMETIC

CROSS REFERENCE TO RELATED APPLICATIONS

This is a U.S. National Phase application under 35 U.S.C. § 371 of International Patent Application No. PCT/JP2018/020149, filed May 25, 2018, which claims priority of Japanese Patent Application No. 2017-108323, filed May 31, 2017. The entire contents of which are hereby incorporated by reference.

TECHNICAL FIELD

The present invention relates to hollow particles having a soft texture property, which is specific to plastic beads, and cosmetics containing the hollow particles.

BACKGROUND

Petroleum-derived synthetic polymers (plastics) are presently utilized in various industries, and support the convenient life in these modern days. Many of synthetic polymers have been developed in a quest for long-term stability. Therefore, synthetic polymers are not degraded in natural environment, causing various environmental problems. One of such problems is that plastic products flowing out to aqueous environment accumulate for an extended period, and have significantly harmful effects on the ecosystems of oceans and lakes. Also, fine plastics having a length of from not more than 5 mm to nano levels, which are called microplastics, are recently considered as another serious problem. Examples of the microplastics include fine particles contained in cosmetic products and the like, small chunks of unprocessed plastic resin, and micro-pieces resulting from the fragmentation of large products floating in the sea.

In recent years, several hundred micrometers-class plastic particles (for example, polyethylene particles) are blended in face washes in order to enhance washing effects. Plastic particles, which have a small true specific gravity, are difficult to remove at sewage treatment plants, resulting in outflow into rivers, oceans, ponds, and the like. Since plastic particles are likely to adsorb chemicals such as pesticides, human bodies possibly have adverse effects due to biological concentration. This issue is also pointed out in the United Nations Environment Programme and the like. Various countries and industrial organizations conduct studies on setting regulations against the issue.

Under such circumstances, inorganic oxide particles, which do not contain organic matter, are proposed. For example, it is known that when porous or non-porous spherical particles including an aggregate of inorganic oxide fine particles coated with a silica layer are used as a filler of cosmetics, there can be obtained cosmetics that are extraordinarily light, soft, and readily spreadable (see, for example, WO 2004/006873 A). It is also known that porous particles with an average particle diameter of 0.5 to 30 μm having excellent surface smoothness are used in order to improve the texture properties of cosmetics (see, for example, JP-A-2009-137806).

Furthermore, hollow particles including a negative-pressure cavity (porosity: 20 to 95% by weight) inside a non-porous shell are known as inorganic oxide particles having high adhesiveness to the skin and a low rough and dry texture property (see, for example, JP-A-2011-256098).

SUMMARY

However, it has been difficult for inorganic oxide particles, which do not contain organic matter, to develop a soft texture property during application. Thus, such inorganic oxide particles could not satisfactorily serve as an alternative to plastic beads.

Therefore, an object of the present invention is to achieve inorganic oxide particles having a soft texture property similar to plastic beads.

The present inventors found that the true specific gravity of particles is a factor causing a soft feel during application, and that the formation of fine convex portions on the surface of particles reduces adhesiveness and provides appropriate fluidity. Based on these findings, inorganic oxide particles having a soft texture property like plastic beads have been achieved.

That is, the inorganic oxide particles according to the present invention are hollow particles including a cavity inside a shell and convex portions with a size of 3 to 100 nm on the surface of the shell and having a true specific gravity of 0.3 to 3.0 g/cm$^3$. The hollow particles have an average particle diameter of 1 to 20 μm and a specific surface area per unit volume calculated by a BET method of not less than 0.5 and less than 60 m$^2$/cm$^3$. According to such particles, there can be obtained a soft texture property and the effect of facilitating uniform spreadability on the skin (that is, high fluidity). Furthermore, the convex portions on the surface of the particles are preferably 5 or more in number per 1 μm$^2$, and preferably have a spherical cap-like shape.

Also, the shell of the hollow particles is preferably non-porous. Therefore, the true specific gravity is preferably not less than 2.2 g/cm$^3$.

Also, the cosmetics according to the present invention contain any one of the above-described hollow particles.

According to the present invention, there can be achieved particles which raise no concern about causing environmental problems and have a soft texture property similar to plastic beads. Therefore, the particles according to the present invention can be reliably used as an alternative to plastic beads.

DETAILED DESCRIPTION

The hollow particles according to the present invention have a balloon structure which includes a cavity inside a shell. The particles include convex portions having a size of 3 to 100 nm on the surface. Also, the particles has a true specific gravity of 0.3 to 3.0 g/cm$^3$ and a specific surface area (m$^2$/cm$^3$) per unit volume calculated by a BET method of not less than 0.5 and less than 60. Furthermore, the particles have an average particle diameter ($d_1$) calculated by laser diffraction of 1 to 20 μm. Such particles can have a soft texture property and appropriate fluidity. When the average particle diameter ($d_1$) is less than 1 μm, adhesiveness increases, which inhibits uniform spreadability on the skin (that is, fluidity is low). On the other hand, when more than 20 μm, the powder of particles feels grainy when touched, with the result that a soft feel decreases. In particular, the average particle diameter is preferably 2 to 8 μm.

Here, the hollow particles are inorganic oxide particles containing silica. That is, the shell of the hollow particles contains a composite oxide such as silica-alumina, silica-zirconia, and silica-titania, or silica. In consideration that the hollow particles are to be blended in cosmetics, amorphous silica particles are suitable.

A preferable range of true specific gravity varies depending on the composition of the particles. For example, when silica is contained in an amount of not less than 99% in the composition, the true specific gravity of the particles is preferably 0.3 to 2.1 g/cm$^3$. When the true specific gravity is not more than 2.1 g/cm$^3$, it is considered that a cavity exists inside, because the specific gravity of silica is 2.2 g/cm$^3$. The shell of the hollow particles having a true specific gravity of not more than 0.3 g/cm$^3$ is thin, and low in strength. Therefore, the particles may be broken due to a mechanical share caused when blended to cosmetics. On the other hand, when the true specific gravity is more than 2.1 g/cm$^3$, a sufficient cavity does not exist. Therefore, a soft texture property is unlikely to be obtained. The true specific gravity of the particles is more preferably 0.5 to 2.0 g/cm$^3$, further preferably 0.7 to 1.8 g/cm$^3$.

When the shell of the hollow particles contains silica-alumina, and the composition ratio (silica/alumina) is 85/15, calculated specific gravity comes to be 2.5 g/cm$^3$. In this case, the true specific gravity is preferably 0.4 to 2.4 g/cm$^3$. Also, when the composition ratio (silica/alumina) is 35/65, the calculated specific gravity comes to be 3.1 g/cm$^3$. Therefore, the true specific gravity of the particles is preferably 0.5 to 3.0 g/cm$^3$. In this way, when the true specific gravity of the particles is lower than theoretical specific gravity calculated from the composition, it demonstrates that a cavity exists inside.

Also, whether or not a cavity exists inside can be estimated from porosity calculated according to the following equation. "porosity=(1−true specific gravity/(theoretical specific gravity calculated from composition of particles))×100" Here, when silica is contained in an amount of not less than 99% in the composition, the porosity of the particles is 5 to 86%.

On the other hand, when the specific surface area of the hollow particles calculated by a BET method is not less than 60 m$^2$/cm$^3$, the hollow particles fit the definition of nanomaterials, and may not be reliably used in applications similar to known plastic beads.

Also, when the size of the convex portions on the surface of the particles is less than 3 nm, adhesiveness is high, which significantly reduces fluidity. On the other hand, when more than 100 nm, adhesiveness is excessively low, which increases the rolling property of the particles. As a result, a desired soft feel is unlikely to be obtained. It is noted that the height of the convex portions is preferably 5 to 60 nm, further preferably 7 to 20 nm. Also, the convex portions having a size of not less than 3 nm preferably are 5 or more in number per 1 μm. When they are 5 or more in number, uniform frictional resistance can be imparted. Furthermore, the convex portions preferably have a spherical cap-like shape. The spherical cap-like shape facilitates uniform control of frictional resistance.

Furthermore, the shell is preferably non-porous. That is, when silica is contained in an amount of not less than 99% in the composition of the particles, the true specific gravity of the shell is preferably 2.2 g/cm$^3$. When the true specific gravity of the shell is less than 2.2 g/cm$^3$, the mechanical strength of the shell decreases, which may cause the particles to be broken due to a mechanical share when blended to cosmetics.

It is noted that when the shell contains a composite oxide such as silica-alumina, preferable true specific gravity becomes higher as the ratio of alumina increases. That is, a true specific gravity of not more than 2.2 g/cm$^3$ is not preferable for the non-porous shell.

Also, when the hollow particles are poured in a dispersion liquid having a refractive index of 1.46 to measure haze, the measured haze is suitably not less than 50%. Since the refractive index of sebum secreted from the skin is around 1.46, an appropriate light diffusion property is not impaired even when the hollow particles are wet with sebum after application to the skin.

Furthermore, when the infrared absorption spectrum of the hollow particles is measured, a ratio ($I_1/I_2$) between maximum absorbance ($I_1$) at 3730 to 3750 cm$^{-1}$ and maximum absorbance ($I_2$) at 1160 to 1260 cm$^{-1}$ is suitably not more than 0.05. As the number of silanol groups (Si—OH) on the surface of the particles decreases, infrared absorbance at 3730 to 3750 cm$^{-1}$ decreases. On the other hand, infrared absorbance at 1160 to 1260 cm$^{-1}$ attributable to Si—O—Si increases. Since silanol groups bind with water, fewer silanol groups lead to lower hydrophilicity. That is, it can be said that the smaller the absorbance ratio ($I_1/I_2$), the lower the hydrophilicity on the surface of the particles. Particles having low hydrophilicity, which is low in adhesiveness to the skin, can develop a soft texture property during application to the skin. It is noted that the absorbance ratio can be reduced by hydrophobizing the surface through a surface treatment with a silane compound or the like or through crushing silanol groups via high-temperature calcination or the like.

<Method of Manufacturing Hollow Particles>

Next, the method of manufacturing the hollow particles according to the present invention will be described.

(Step A)

First, a sol containing spherical inorganic oxide fine particles dispersed in water is prepared. The sol desirably contains the inorganic oxide fine particles in an amount of 1 to 30% by weight in terms of solid content. Here, the inorganic oxide fine particles are fine particles that contain silica as an ingredient. Examples of such fine particles may include fine particles of a composite oxide such as silica-alumina, silica-zirconia, and silica-titania, and silica fine particles. In consideration that the fine particles are to be blended to cosmetics, amorphous silica particles are suitable. It is noted that manufacturing conditions do not need to be changed depending on a difference in the composition of the fine particles.

To this inorganic oxide sol, a silicic acid liquid having a silica concentration of 1 to 50% by weight is added to prepare a slurry. The inorganic oxide sol and the silicic acid liquid are mixed such that a solid content weight ratio (I/II) between an inorganic oxide ingredient (I) of the sol and a silica ingredient (II) of the silicic acid liquid becomes 0.05 to 1.

The silicic acid liquid to be used is obtained by treating an aqueous silicate solution with cation exchange resin for dealkalization (such as removal of Na ions). Examples of the silicate include alkali metal silicates such as sodium silicate (water glass) and potassium silicate, and organic base silicates such as quaternary ammonium silicate.

(Step B)

With the slurry obtained in step A, granulation is performed by a known spray drying method. For example, a spray drying method by a spray dryer includes spraying a spray liquid (slurry) into a hot air stream at a speed of 1 to 3 L/h. This allows hollow particles to be obtained. In the spraying, the temperature of hot air is preferably 70 to 600° C. in inlet temperature and 40 to 300° C. in outlet temperature. When the inlet temperature is less than 70° C., drying of solid content becomes insufficient. Also, when more than 600° C., the shape of the particles may distort. Also, when the outlet temperature is less than 40° C., the drying degree of solid content is poor, which facilitates the adherence of the particles to the inside of an apparatus. The obtained particles may be washed, dried, or calcined as necessary.

According to such steps, there can be obtained particles (that is, hollow particles) having a balloon structure which includes a cavity formed inside a shell. Furthermore, the hollow particles include convex portions having a size of 3 to 100 nm on the surface, and have a true specific gravity of 0.3 to 3.0 g/cm$^3$. Here, it is considered that the shell contains a silicic acid ingredient contained in the slurry, and that the convex portions formed on the shell contain inorganic oxide fine particles. Therefore, an average particle diameter ($d_2$) of the inorganic oxide fine particles is preferably 6 to 200 nm. When the average particle diameter is more than 200 nm, the convex portions on the surface of the particles become excessively large, which inhibits a desired texture property from being obtained. On the other hand, when the average particle diameter is less than 6 nm, the inorganic oxide fine particles are low in stability, which is not preferable from industrial aspects. The average particle diameter is preferably 10 to 120 nm, particularly preferably 14 to 90 nm. Furthermore, the particle diameter variance coefficient (CV) of the inorganic oxide fine particles is preferably within 10%.

While fine particles having the above-described composition are used as the inorganic oxide fine particles, the silicic acid liquid may contain a metal ingredient such as alumina, zirconia, and titania. That is, the adjustment of the composition of the inorganic oxide sol and the composition of the silicic acid liquid allows the hollow particles to have various compositions. For example, there can be easily obtained: particles including a shell and convex portions both containing silica, particles including a shell and convex portions both containing silica-alumina, and particles including a shell and convex portions each containing a different silica-based material.

It is noted that hollow particles containing a silica ingredient generated from a plant-derived raw material are preferable from the viewpoint of achieving a sustainable society. Also, needs for organic cosmetics are growing overseas such as in Europe and the United States from the viewpoint of the harmony with environment and the involvement in safety. Raw materials of organic cosmetics are defined in ISO16128-1 (Guidelines on technical definitions and criteria for natural And organic cosmetic ingredients and products, Part 1: Definitions for ingredients). Silica sand, which is heavily used as a silica source, is classified into mineral ingredients. However, a plant-derived silica ingredient is classified into naturally-derived ingredients. Therefore, silica sand can meet the needs.

A plant-derived silica ingredient is richly contained in gramineous plants, and can be extracted from chaff and ears of rice. It is known that highly pure silica can be obtained by, for example, a calcination method disclosed in JP-A-7-196312 or a pressurized hydrothermal method disclosed in JP-A-2002-265257. The plant-derived silica ingredient obtained in this manner can be dissolved in sodium hydroxide to prepare sodium silicate. Thereafter, silica-based particles can be prepared according to a method known in the art.

<Cosmetics>

Unlike known inorganic particles such as silica particles, cosmetics including the hollow particles according to the present invention can have not only a rolling feel, persistence of a rolling feel, and uniform spreadability, but also typical texture properties required of texture improvers of cosmetics, that is a soft feel and a moist feel specific to plastic beads.

EXAMPLES

Hereinafter, examples of the use of a silica sol as an inorganic oxide sol will be specifically described.

Example 1

Cation exchange was performed to a sol (commercially available product: manufactured by JGC Catalysts and Chemicals Ltd.; Cataloid SI-30, silica concentration 30% by weight) in which silica fine particles having an average particle diameter of 11 nm were dispersed in water, in order to adjust the pH to 2.0. Accordingly, there was obtained a silica sol having a solid content concentration of 30% by weigh as an inorganic oxide sol. This silica sol contains silica fine particles as inorganic oxide fine particles.

On the other hand, JIS No. 3 water glass was diluted with pure water, and thereafter, cation exchange was performed to prepare a silicic acid liquid having a silica concentration of 4.5% by weight. To 2000 g of this silicic acid liquid, 75 g of the above-described inorganic oxide sol was added. At this time, a solid content weight ratio (I/II) between a silica ingredient (I) of the inorganic oxide sol and a silica ingredient (II) of the silicic acid liquid is "22.5/90," that is, "20/80". Thus, there was obtained a dispersion slurry having an inorganic oxide sol concentration of 1.1% by weight, a water glass-derived silica concentration of 4.3% by weight, and a solid content concentration of 5.4% by weight.

Spray drying was performed with this dispersion slurry as a spray liquid using a spray dryer (manufactured by NIRO Co., NIRO-ATMIZER). That is, spray drying was performed by supplying the slurry from one of a two-fluid nozzles at a flow rate of 2 L/h and gas from the other at a pressure of 0.15 Mpa into a dry air stream set at an inlet temperature of 200° C. and an outlet temperature of 50 to 55° C. Thus, a dry powder was obtained.

This dry powder was calcined at 600° C. for 4 hours. Thereafter, a dry sieve treatment was performed to obtain a powder of hollow particles. The physical properties of this powder are illustrated in Table 2. Also, the preparation conditions of the particles are illustrated in Table 1. The measurement values in the table were measured by the following methods.

(1) Average Particle Diameters (Di) and ($d_2$), and Particle Diameter Variance Coefficient (CV)

The particle size distribution of the particles of each example was measured by laser diffractometry. This particle size distribution was used to calculate an average particle diameter ($d_1$) of the hollow particles, and an average particle diameter ($d_2$) and a particle diameter variance coefficient (CV) of the inorganic oxide fine particles. In this calculation, a median value obtained from the particle size distribution was defined as an average particle diameter. It is noted that the particle size distribution was measured using a laser diffraction/scattering particle diameter distribution measuring device LA-950v2 (manufactured by Horiba, Ltd.).

(2) True Specific Gravity of Particles

Into a magnetic crucible (B-2 type), about 30 ml of a powder of hollow particles is sampled, and dried at 300° C. for 1 hour. Thereafter, the dried powder is poured in a desiccator, and cooled to room temperature. Next, 15 ml of the resultant product was sampled, and a true specific gravity was measured using a fully automated pycnometer (manufactured by Quantachrome Instruments: Ultrapyc 1200e).

(3) True Specific Gravity of Shell

A powder of hollow particles was poured into an agate mortar, and pulverized using a pestle. The true specific gravity of the obtained pulverized product was measured. The pulverization caused the hollow particles to be broken, and a cavity inside was lost. Therefore, the true specific gravity of the pulverized product was defined as the true specific gravity of a shell.

(4) Specific Surface Area

Into a magnetic crucible (B-2 type), about 30 ml of a powder of hollow particles was sampled, and dried at 300° C. for 1 hour. Thereafter, the dried powder was poured in a desiccator, and cooled to room temperature. Next, 1.0 g of the resultant product was sampled, and a specific surface area ($m^2/g$) was measured by a BET method using a fully automated surface area measuring device (manufactured by Yuasa Ionics Co., Ltd., Multisorb 12). Then, the specific surface area was converted into a specific surface area per unit volume on the assumption that the specific gravity of silica is 2.2 $g/cm^3$.

(5) Pore Volume

Into a crucible, 10 g of a powder of hollow particles was sampled, and dried at 105° C. for 1 hour. Thereafter, the dried powder was poured in a desiccator, and cooled to room temperature. Subsequently, 1.0 g of the sample was poured into a well-washed cell, and nitrogen was adsorbed using a nitrogen adsorber. The pore volume was calculated according to the following equation.

$$\text{Pore volume (ml/g)} = 0.001567 \times (V - Vc)/W$$

In the equation, V represents an adsorption amount (ml) in a standard state at a pressure of 735 mmHg, Vc represents a volume (ml) of a cell blank at a pressure of 735 mmHg, and W represents a mass (g) of a sample. Also, a density ratio between nitrogen gas and liquid nitrogen is defined to be 0.001567.

(6) Size of Convex Portions

To about 1 g of epoxy resin (EPO-KWICK manufactured by BUEHLHER), 0.1 g of a powder of hollow particles was uniformly mixed. The mixture was cured at normal temperature. Thereafter, a cross-section treatment of a 20 μm area was performed using an FIB processor (manufactured by Hitachi, Ltd., FB-2100) to prepare a sample of a section having a thickness of 100 to 200 nm. Subsequently, a TEM picture of this sample was taken at a magnification of 100000 under the condition of an accelerating voltage of 200 kV, using a transmission electron microscope (manufactured by Hitachi, Ltd., HF-2200). Furthermore, for optional 10 TEM pictures, a difference between a circumscribed circle and an inscribed circle on the surface of the particles was measured. The average value of the measurements was defined as the size of the convex portions on the surface of the hollow particles.

(7) Shape and the Number of Convex Portions of Hollow Particles

A SEM picture taken using a scanning electron microscope was observed, and the number of convex portions of hollow particles was evaluated. A SEM picture of randomly selected 100 to 200 particles was analyzed to check whether or not the shape of the convex portions was a spherical cap. Also, the convex portions having a size of not less than 5 nm were counted to check whether or not five or more convex portions were formed on a 1 $\mu m^2$ projected portion.

(8) Haze in Dispersion Liquid (Refractive Index 1.46)

There were mixed 9.0 g of distilled water and 91.0 g of glycerin (manufactured by Kanto Chemical Co., Inc., special grade) to prepare an aqueous glycerin solution having a refractive index of 1.46. To 7.0 g of this aqueous glycerin solution, 3.0 g of a powder of hollow particles was added, and dispersed by irradiation with ultrasonic waves (US-2KS manufactured by SND Co., Ltd.) for 30 minutes. The haze of the obtained dispersion liquid was measured using a color/turbidity simultaneously measuring device (300 A manufactured by Nippon Denshoku Industries Co., Ltd.), and the measured value was defined as the haze of the hollow particles.

(9) $SiO_2$ Quantitative Value

In a platinum dish, 0.2 g of a powder of hollow particles was precisely weighed. To the weighed powder, 10 ml of sulfuric acid and 10 ml of hydrofluoric acid were added. The mixture was heated on a sand bath until white smoke of sulfuric acid was produced. After cooling, about 50 ml of water was added, and heated to dissolve the powder. After cooling, the resultant product was diluted with 200 ml of water to obtain a test solution. For this test solution, the composition rate of the hollow particles was calculated using an inductively coupled plasma emission spectroscopic analyzer (manufactured by Shimadzu Corporation, ICPS-8100, analysis software ICPS-8000).

(10) Absorbance Ratio

The infrared absorption spectrum of hollow particles was measured using FT-IR6300 (manufactured by Jasco Corporation) to create a graph illustrating a relationship between a wave number ($cm^{-1}$) and an absorbance calculated according to the Kubelka-Munk formula. From the obtained graph, a maximum absorbance ($I_1$) at 3730 to 3750 $cm^{-1}$ and a maximum absorbance ($I_2$) at 1160 to 1260 $cm^{-1}$ were read, and an absorbance ratio ($I_1/I_2$) was calculated.

TABLE 1

| | Inorganic oxide sol (I) | | | | | Dispersion slurry | | | | | |
| | Inorganic oxide fine particles | | | Solid | Silicic acid liquid (II) | | Solid | | Spray drying conditions | | Calcination conditions |
| | Type of silica ingredient | Average fine particle diameter ($d_2$) (nm) | CV (%) | content concentration (% by weight) | Type of silica ingredient | Silica concentration (% by weight) | Solid content weight ratio (I/II) | content concentration (% by weight) | Spray-speed (L/Hr) | Spray-pressure (MPa) | Inlet temperature (° C.) | Temperature (° C.) | Duration (Hr) |
|---|---|---|---|---|---|---|---|---|---|---|---|---|---|
| Example 1 | A | 11 | 9.0 | 30 | F | 4.5 | 20/80 | 5.4 | 2 | 0.15 | 180 | 600 | 4 |
| Example 2 | B | 160 | 8.5 | 16 | F | 4.5 | 50/50 | 7.0 | 2 | 0.15 | 180 | 600 | 4 |
| Example 3 | A | 11 | 9.0 | 30 | F | 4.5 | 20/80 | 5.4 | 2 | 0.30 | 180 | 600 | 4 |
| Example 4 | A | 11 | 9.0 | 30 | F | 4.5 | 20/80 | 5.4 | 2 | 0.60 | 180 | 600 | 4 |
| Example 5 | A | 11 | 9.0 | 30 | (1) | 18 | 20/80 | 19.6 | 2 | 0.60 | 380 | 1000 | 3 |

TABLE 1-continued

| | Inorganic oxide sol (I) | | | | Dispersion slurry | | | | | | | |
|---|---|---|---|---|---|---|---|---|---|---|---|---|
| | Inorganic oxide fine particles | | Solid | Silicic acid liquid (II) | | Solid | | Spray drying conditions | | | Calcination conditions | |
| | | Average | content | | Silica | | content | | | | | |
| | Type of | fine | concen- | | concen- | | concen- | | | Inlet | | |
| | silica ingre- dient | particle diameter ($d_2$) (nm) | CV (%) | tration (% by weight) | Type of silica ingredient | tration (% by weight) | Solid content weight ratio (I/II) | tration (% by weight) | Spray- speed (L/Hr) | Spray- pressure (MPa) | temper- ature (° C.) | Temper- ature (° C.) | Dura- tion (Hr) |
| Example 6 | A | 11 | 9.0 | 30 | F | 4.5 | 50/50 | 7.8 | 2 | 0.15 | 180 | 600 | 4 |
| Example 7 | C | 80 | 7.0 | 30 | F | 4.5 | 40/60 | 6.8 | 2 | 0.15 | 180 | 600 | 4 |
| Example 8 | A | 11 | 9.0 | 30 | F | 4.5 | 20/80 | 5.4 | 2 | 0.15 | 180 | 1000 | 3 |
| Example 9 | E | 20 | 9.0 | 23 | F | 4.5 | 50/50 | 7.5 | 2 | 0.15 | 180 | 600 | 4 |
| Comparative Example 1 | D | 5 | 7.0 | 10 | F | 4.5 | 20/80 | 5.1 | 2 | 0.15 | 180 | 600 | 4 |
| Comparative Example 2 | A | 11 | 9.0 | 30 | F | 4.5 | 95/5 | 23.4 | 2 | 0.15 | 180 | 600 | 4 |
| Comparative Example 3 | A | 11 | 9.0 | 30 | F | 4.5 | 50/50 | 7.8 | 4 | 0.05 | 180 | 600 | 4 |
| Comparative Example 4 | A | 11 | 9.0 | 30 | F | 4.5 | 1/99 | 4.5 | 2 | 0.15 | 180 | 600 | 4 |
| Comparative Example 5 | — | — | — | — | F | 4.5 | 0/100 | 4.5 | 2 | 0.15 | 180 | 600 | 4 |

Silica ingredient A: Cataloid SI-30 (average particle diameter 11 nm) manufactured by JGC Catalysts and Chemicals Ltd.
Silica ingredient B: SS-160 (average particle diameter 160 nm) manufactured by JGC Catalysts and Chemicals Ltd.
Silica ingredient C: Cataloid SI-80P (average particle diameter 80 nm) manufactured by JGC Catalysts and Chemicals Ltd.
Silica ingredient D: Cataloid SI-550 (average particle diameter 5 nm) manufactured by JGC Catalysts and Chemicals Ltd.
Silica Ingredient E: USBB-120 (average particle diameter 20 nm) manufactured by JGC Catalysts and Chemicals Ltd.
Silica ingredient F: silicic acid liquid (silicate (1) is desalted)
Silicate (1): JIS3 water glass

TABLE 2

| | Hollow particles | | | | | | | | | | |
|---|---|---|---|---|---|---|---|---|---|---|---|
| | Average particle size ($d_1$) μm | True specific gravity g/cm³ | True specific gravity of shell g/cm³ | Specific surface area m²/cm³ | Pore Volume ml/g | Convex portion volume | | | Haze % | SiO₂ quantitative value % | Absor- bance ratio |
| | | | | | | Size nm | Shape | Number/ μm³ | | | |
| Example 1 | 7.1 | 2.1 | 2.2 | 3 | Detection limit or less *¹ | 5 | Spherical cap | 5 or more | 52 | 99.7 | 0.015 |
| Example 2 | 7.0 | 2.1 | 2.2 | 2 | Detection limit or less *¹ | 79 | Spherical cap | 5 or more | 58 | 99.7 | 0.010 |
| Example 3 | 4.0 | 2.1 | 2.2 | 3 | Detection limit or less *¹ | 5 | Spherical cap | 5 or more | 53 | 99.7 | 0.014 |
| Example 4 | 2.0 | 2.1 | 2.2 | 3 | Detection limit or less *¹ | 5 | Spherical cap | 5 or more | 54 | 99.7 | 0.014 |
| Example 5 | 9.0 | 0.6 | 2.2 | 2 | Detection limit or less *¹ | 15 | Spherical cap | 5 or more | 68 | 99.7 | 0.008 |
| Example 6 | 7.5 | 2.1 | 2.2 | 3 | Detection limit or less *¹ | 5 | Spherical cap | 5 or more | 55 | 99.7 | 0.010 |
| Example 7 | 7.0 | 2.1 | 2.2 | 2 | Detection limit or less *¹ | 40 | Spherical cap | 5 or more | 56 | 99.8 | 0.010 |
| Example 8 | 6.8 | 2.1 | 2.2 | 2 | Detection limit or less *¹ | 5 | Spherical cap | 5 or more | 51 | 99.7 | 0.002 |
| Example 9 | 7.5 | 2.3 | 2.5 | 3 | Detection limit or less *¹ | 10 | Spherical cap | 5 or more | 60 | 94.9 | 0.010 |
| Comparative Example 1 | 7.0 | 2.1 | 2.2 | 4 | Detection limit or less *¹ | 1 | Spherical cap | 0 | 31 | 99.7 | 0.015 |
| Comparative Example 2 | 9.9 | 2.2 | 2.2 | 242 | 0.14 | 5 | Spherical cap | 5 or more | 22 | 99.7 | 0.070 |
| Comparative Example 3 | 23.5 | 2.2 | 2.2 | 8 | Detection limit or less *¹ | 5 | Spherical cap | 5 or more | 40 | 99.7 | 0.015 |
| Comparative Example 4 | 6.8 | 2.1 | 2.2 | 0.2 | Detection limit or less *¹ | — | Convex portion not detected | 0 | 50 | 99.7 | 0.010 |

TABLE 2-continued

| | Hollow particles | | | | | | | | | | |
|---|---|---|---|---|---|---|---|---|---|---|---|
| | Average particle size ($d_1$) μm | True specific gravity g/cm³ | True specific gravity of shell g/cm³ | Specific surface area m²/cm³ | Pore Volume ml/g | Convex portion volume | | | Haze % | SiO₂ quantitative value % | Absorbance ratio — |
| | | | | | | Shape Size nm — | Number/ μm³ | | | | |
| Comparative Example 5 | 6.8 | 2.1 | 2.2 | 0.1 | Detection limit or less *¹ | — | Convex portion not detected | 0 | 50 | 99.9 | 0.015 |

*¹ Detection limit 0.01 ml/g

Example 2

In Example 1, SS-160 (manufactured by JGC Catalysts and Chemicals Ltd., average particle diameter 160 nm) was used instead of a silica sol (SI-30) to prepare an inorganic oxide sol having a solid content concentration of 16% by weight. To this sol, the silicic acid liquid of Example 1 was added such that the solid content weight ratio illustrated in Table 1 was achieved, and thus a dispersion slurry was obtained. This dispersion slurry was used to prepare and measure a powder of hollow particles in the same manner as in Example 1.

Example 3

In this Example, the gas supply pressure of the two-fluid nozzles was set to be 0.3 Mpa. Otherwise, a powder of hollow particles was prepared and measured in the same manner as in Example 1.

Example 4

In this Example, the gas supply pressure of the two-fluid nozzles was set to be 0.6 Mpa. Otherwise, a powder of hollow particles was prepared and measured in the same manner as in Example 1.

Example 5

In this Example, JIS3 water glass was used as the silicic acid liquid (II) without performing cation exchange, and the inlet temperature during spray drying was set to be 380° C. Otherwise, a dry powder was prepared in the same manner as in Example 1. Into an aqueous sulfuric acid solution (25%), 100 g of the obtained dry powder was suspended for neutralization. The slurry obtained by neutralization was filtered through a quantitative filter paper sheet (No. 2, manufactured by Advantec Toyo Kaisha, Ltd.) using a Buchner funnel (3.2 L, manufactured by SEKIYARIKA Co., Ltd.). Thereafter, the obtained product was repeatedly washed with pure water, and thus a cake-like substance was obtained. This cake-like substance was dried (120° C., 16 hours) to obtain a dry powder a. Thereafter, the dry powder a was calcined at 1000° C. for 3 hours, and subjected to a dry sieve treatment to obtain a powder. This powder was measured in the same manner as in Example 1.

Example 6

In this Example, the solid content weight ratio (I/II) between the silica ingredient (I) of the inorganic oxide sol and the silica ingredient (II) of the silicic acid liquid in the dispersion slurry was changed to 50/50. Otherwise, a powder of hollow particles was prepared and measured in the same manner as in Example 1.

Example 7

In Example 1, SI-80P (manufactured by JGC Catalysts and Chemicals Ltd., average particle diameter 80 nm) was used instead of the silica sol (SI-30) to prepare an inorganic oxide sol. To this sol, the silicic acid liquid of Example 1 was added such that the solid content weight ratio illustrated in Table 1 was achieved. With this obtained dispersion slurry, a powder of hollow particles was prepared and measured in the same manner as in Example 1.

Example 8

In this Example, calcination conditions were set to be 1000° C. and 3 hours. Otherwise, a powder of hollow particles was prepared and measured in the same manner as in Example 1.

Example 9

In Example 1, USBB-120 (manufactured by JGC Catalysts and Chemicals Ltd., average particle diameter 5 nm, composition: silica/alumina=70/30) was used instead of the silica sol (SI-30) to prepare an inorganic oxide sol having a solid content concentration of 23% by weight. To this sol, the silicic acid liquid of Example 1 was added such that the solid content weight ratio illustrated in Table 1 was achieved. With this obtained dispersion slurry, a powder of hollow particles was prepared and measured in the same manner as in Example 1.

Comparative Example 1

In Example 1, SI-550 (manufactured by JGC Catalysts and Chemicals Ltd., average particle diameter 5 nm) was used instead of the silica sol (SI-30) to prepare an inorganic oxide sol having a solid content concentration of 10% by weight. To this sol, the silicic acid liquid of Example 1 was added such that the solid content weight ratio illustrated in Table 1 was achieved. With this obtained dispersion slurry, a powder of particles was prepared and measured in the same manner as in Example 1.

Comparative Example 2

Mixing was performed such that the solid content weight ratio (I/II) between the silica ingredient (I) of the inorganic oxide sol and the silica ingredient (II) of the silicic acid liquid in the dispersion slurry became 95/5. Otherwise, a powder of particles was prepared and measured in the same manner as in Example 1.

Comparative Example 3

In this Comparative Example, mixing was performed such that the solid content weight ratio (I/II) between the silica ingredient (I) of the inorganic oxide sol and the silica ingredient (II) of the silicic acid liquid in the dispersion slurry became 50/50. Furthermore, the gas supply pressure of the two-fluid nozzles was set to be 0.05 MPa, and the spray speed was set to be 4 L/h. Otherwise, a powder of particles was prepared and measured in the same manner as in Example 1.

Comparative Example 4

In this Comparative Example, mixing was performed such that the solid content weight ratio (I/II) between the silica ingredient (I) of the inorganic oxide sol and the silica ingredient (II) of the silicic acid liquid in the dispersion slurry became 1/99. Otherwise, a powder of particles was prepared and measured in the same manner as in Example 1.

Comparative Example 5

In this Comparative Example, a dispersion slurry was prepared with only the silicic acid liquid, without using the silica sol. Otherwise, a powder of particles was prepared and measured in the same manner as in Example 1.

<Application to Cosmetics>

Twenty specialized panelists conducted a sensory test on the powders of particles obtained in Examples and Comparative Examples. In the test, the following seven evaluation items (texture properties) were studied by hearing: a smooth and dry feel, a moist feel, a rolling feel, uniform spreadability, adhesiveness to the skin, persistence of a rolling feel, and a soft feel. The results were evaluated based on the following evaluation criteria (a). Furthermore, evaluation points scored by the panelists were totaled, and the texture of the particles was evaluated based on the following evaluation criteria (b).

Evaluation Point Criteria (a)
  5 points: Very superior
  4 points: Superior
  3 points: Average
  2 points: Inferior
  1 point: Very inferior Evaluation Criteria (b)
  Excellent: 80 points or more in total
  Good: 60 points or more and less than 80 points in total
  Fair: 40 points or more and less than 60 points in total
  Poor: 20 points or more and less than 40 points in total
  Bad: less than 20 points in total The results are illustrated in Table 3. As understood from the table, the powders of Examples are extremely superior as a texture improver for cosmetics, whereas the powders of Comparative Examples are not suitable as a texture improver.

TABLE 3

|  | Smooth and dry feel | Moist feel | Rolling feel | Uniform spreadability | Adhesiveness to skin | Persistence of rolling feel | Soft feel |
|---|---|---|---|---|---|---|---|
| Example 1 | Excellent | Good | Good | Good | Good | Good | Good |
| Example 2 | Good | Good | Fair | Good | Fair | Excellent | Good |
| Example 3 | Good | Good | Fair | Fair | Good | Fair | Good |
| Example 4 | Poor | Excellent | Fair | Poor | Excellent | Fair | Good |
| Example 5 | Good | Excellent | Excellent | Good | Fair | Excellent | Excellent |
| Example 6 | Good | Fair | Excellent | Excellent | Poor | Excellent | Poor |
| Example 7 | Good | Good | Fair | Good | Fair | Good | Good |
| Example 8 | Good | Excellent | Fair | Good | Excellent | Good | Excellent |
| Example 9 | Good | Excellent | Poor | Fair | Excellent | Good | Good |
| Comparative Example 1 | Poor | Good | Poor | Poor | Good | Poor | Good |
| Comparative Example 2 | Excellent | Bad | Excellent | Fair | Bad | Good | Bad |
| Comparative Example 3 | Good | Poor | Excellent | Fair | Bad | Excellent | Bad |
| Comparative Example 4 | Bad | Excellent | Bad | Bad | Excellent | Bad | Good |
| Comparative Example 5 | Bad | Excellent | Bad | Bad | Excellent | Bad | Excellent |

[Use Feels of Powder Foundations]

The powder of particles of each Example (or each Comparative Example) and other ingredients (2) to (9) at the blend ratios (% by weight) illustrated in Table 4 were poured into a mixer. The mixture was stirred to be uniformly mixed. Next, cosmetic ingredients (10) to (12) were poured into this mixer. The mixture was stirred to be further uniformly mixed. The obtained cake-like substance was pulverized. Thereafter, about 12 g of the pulverized substance was taken, and placed in a 46 mm×54 mm×4 mm square metal dish for press molding. Twenty specialized panelists conducted a sensory test on this obtained powder foundation. In the test, the following six evaluation items were studied by hearing: (i) uniform spreadability, a moist feel, and smoothness during application onto the skin, and (ii) uniformity of a cosmetic film, a moist feel, and softness after application to the skin. The results are evaluated based on the above-described evaluation point criteria (a). Also, evaluation points scored by the panelists were totaled, and the use feels of the foundation was evaluated based on the above-described evaluation criteria (b). The results are illustrated in Table 5.

TABLE 4

| | Cosmetic ingredients constituting powder foundation | Blend amount/weight (%) |
|---|---|---|
| (1) | Powder according to Example or Comparative Example | 10.0 |
| (2) | Sericite (silicon treatment) | 40.0 |
| (3) | Talc (silicon treatment) | 29.0 |
| (4) | Mica (silicon treatment) | 5.0 |
| (5) | Titanium oxide (silicon treatment) | 7.0 |
| (6) | Yellow iron oxide (silicon treatment) | 1.2 |
| (7) | Red iron oxide (silicon treatment) | 0.4 |
| (8) | Black iron oxide (silicon treatment) | 0.2 |
| (9) | Methyl paraben | 0.2 |
| (10) | Dimethicone | 4.0 |
| (11) | Liquid paraffin | 2.0 |
| (12) | Glyceryl tri 2-ethylhxanoate | 1.0 |

TABLE 5

| | During application | | | After application | | |
|---|---|---|---|---|---|---|
| | Uniform spreadability | Moist feel | Smoothness | Uniformity of film | Moist feel | Softness |
| Example 1 (Cosmetic A) | Excellent | Good | Good | Excellent | Good | Good |
| Example 2 (Cosmetic B) | Good | Fair | Good | Excellent | Good | Good |
| Example 3 (Cosmetic C) | Good | Excellent | Excellent | Excellent | Excellent | Excellent |
| Comparative Example 1 (Cosmetic a) | Poor | Good | Good | Bad | Fair | Good |
| Comparative Example 2 (Cosmetic b) | Good | Bad | Poor | Good | Poor | Bad |
| Comparative Example 4 (Cosmetic c) | Bad | Good | Good | Bad | Poor | Good |

It was found that the cosmetics A to C of Examples 1, 2, and 5 have very excellent use feels both during and after application. However, it was found that the cosmetics a to c of Comparative Examples 1, 2, and 4 have unfavorable use feels.

It is noted that the hollow particles obtained in the above-described Examples are to be blended with various cosmetic ingredients exemplified below.

Olive oil, rapeseed oil, and beef tallow as oils and fats. Jojoba oil, carnuba wax, candelilla wax, and beeswax as waxes. Paraffin, squalane, synthetic and vegetable squalane, α-olefin oligomers, microcrystalline wax, pentane, and hexane as hydrocarbons. Stearic acid, myristic acid, oleic acid, and α-hydroxy acid as fatty acids. Isostearyl alcohol, octyldodecanol, lauryl alcohol, ethanol, isopropanol, butyl alcohol, myristyl alcohol, cetanol, stearyl alcohol, and behenyl alcohol as alcohols. Alkyl glyceryl ethers, isopropyl myristate, isopropyl palmitate, ethyl stearate, ethyl oleate, cetyl laurate, and decyl oleate as esters. Ethylene glycol, triethylene glycol, polyethylene glycol, propylene glycol, glycerin, and diglycerin as polyhydric alcohols. Sorbitol, glucose, sucrose, and trehalose as saccharides. Methyl polysiloxane, methyl hydrogen polysiloxane, methyl phenyl silicone oil, various modified silicone oils, and cyclic dimethyl silicon oil as silicone oil. Silicone gel crosslinked by silicone-based and/or other organic compounds. Various nonionic, cationic, and anionic surfactants. Fluorine oil such as perfluoropolyether. Various polymers such as gum arabic, carrageenan, agar, xanthan gum, gelatin, alginic acid, guar gum, albumin, pullulan, carboxyvinyl polymers, cellulose and derivatives thereof, polyacrylic acid amide, sodium polyacrylate, and polyvinyl alcohol. Animal or plant extracts. Amino acid and peptides. Vitamins. UV protectors based on cinnamic acid such as octyl paramethoxycinnamate, salicylic acid, benzoic acid ester, urocanic acid, benzophenone, and the like. Antiseptic and preservative agents. Antioxidants. Modified or unmodified clay minerals. Solvents such as butyl acetate, acetone, and toluene. Various organic pigments and dyes. Water. Flavors. Titanium oxide, zinc oxide, aluminum oxide, aluminum hydroxide, red iron oxide, yellow iron oxide, black iron oxide, cerium oxide, zirconium oxide, silica, mica, talc, sericite, boron nitride, barium sulfate, mica titanium having peal-like gloss, each having various particle diameters, particle diameter distributions, and shapes, and composites thereof. Here, the surface of inorganic compounds such as titanium oxide and zinc oxide may be previously subjected to a silicone treatment, a fluorine treatment, a metal soap treatment, or the like.

Also, resin particles such as methyl polyacrylate, nylon, silicone resin, silicone rubber, polyethylene, polyester, and polyurethane may be contained. Furthermore, as ingredients having whitening effects, there may be contained arbutin, kojic acid, vitamin C, sodium ascorbate, magnesium ascorbate phosphate, ascorbyl dipalmitate, glucoside ascorbate, other ascorbic acid derivatives, placenta extracts, sulfur, plant extracts such as oil-soluble licorice extracts and mulberry extracts, linolic acid, linoleic acid, lactic acid, and tranexamic acid.

Also, as ingredients having rough skin remedying effects, there may be contained: active ingredients having anti-aging effects such as vitamin C, carotinoid, flavonoid, tannin, caffeic acid derivatives, lignan, saponin, retinoic acid and retinoic acid structural analogs, N-acetylglucosamine, and α-hydroxy acid; polyhydric alcohols such as glycerin, propylene glycol, and 1, 3-butylene glycol; saccharides such as saccharide isomerate, trehalose, and pullulan; biopolymers such as sodium hyaluronate, collagen, elastin, chitin/chitosan, and sodium chondroitin sulphate; amino acid, betaine, ceramide, sphingolipid, ceramide, cholesterol and derivatives thereof, ε-aminocaproic acid, glycyrrhizic acid, and various vitamins.

Furthermore, there may be blended cosmetic ingredients described in the Japanese Standards of Quasi-drug Ingredients 2006 (issued by Yakuji Nippo, Limited, Jun. 16, 2006), International Cosmetic Ingredient Dictionary and Handbook (issued by The Cosmetic. Toiletry, and Fragrance Association, Eleventh Edition, 2006), and the like.

Such cosmetics can be manufactured by methods known in the art. The cosmetics are used in various forms such as powders, cakes, pencils, sticks, creams, gels, mousse, liquids, and creams. Specific examples of the cosmetics may include washing cosmetics (such as soaps, cleansing foams, and make-up remover creams), skincare cosmetics (cosmetics for moisture retention and skin roughness prevention, acne, cuticle care, massaging, wrinkle and sag treatments, dullness and shadow treatments, UV care, whitening, and antioxidation care), base makeup cosmetics (powder foundations, liquid foundations, cream foundations, mousse foundations, pressed powders, and makeup bases), point makeup cosmetics (eyeshadows, eyebrow makeup, eyeliners, mascaras, and lipsticks), hair-care cosmetics (cosmetics for hair growth, dandruff prevention, itch prevention, washing, conditioning/hair styling, perming or waving, and hair coloring or bleaching), body-care cosmetics (cosmetics for washing, sunscreening, hand roughness prevention, slimming, blood circulation improvement, itch suppression, deodorization, sweat control, and body hair care, repellents, body powders, and the like), fragrance cosmetics (perfume, eau de parfum, eau de toilette, eau de cologne, shower cologne, solid perfume, body lotion, and bath oil), and oral care products (toothpastes and mouthwashes).

The invention claimed is:

1. Hollow particles with an average particle diameter ($d_1$) of 1 to 20 μm having a balloon structure which includes a cavity inside a shell,
    the particles comprising:
        a true specific gravity of 0.3 to 3.0 g/cm$^3$,
        a specific surface area per unit volume obtained by a BET method of not less than 0.5 m$^2$/cm$^3$ and less than 60 m$^2$/cm$^3$,
        convex portions with a size of 3 to 100 nm on a surface of the particles, and
        the convex portions comprise a spherical cap-like shape;
    wherein the shell comprises silica.

2. The hollow particles according to claim 1, wherein the convex portions are 5 or more in number per 1 μm$^2$.

3. The hollow particles according to claim 1, wherein the shell has a true specific gravity of not less than 2.2 g/cm$^3$.

4. The hollow particles according to claim 1, wherein a haze of the hollow particles in a dispersion liquid having a refractive index of 1.46 is not less than 50%.

5. Cosmetics containing the hollow particles according to claim 1.

* * * * *